(12) United States Patent
Rake et al.

(10) Patent No.: US 6,936,035 B2
(45) Date of Patent: Aug. 30, 2005

(54) PATIENT CONTROLLED DRUG ADMINISTRATION DEVICE

(75) Inventors: Kenneth Wayne Rake, Laguna Nigel, CA (US); Eric Mabry, Trabuco Canyon, CA (US)

(73) Assignee: I-Flow Corporation, Lake Forest, CA (US)

(*) Notice: Subject to any disclaimer, the term of this patent is extended or adjusted under 35 U.S.C. 154(b) by 229 days.

(21) Appl. No.: 10/335,310

(22) Filed: Dec. 31, 2002

(65) Prior Publication Data

US 2004/0127860 A1 Jul. 1, 2004

(51) Int. Cl.$^7$ ............................................... A61M 5/00
(52) U.S. Cl. ............................................................ 604/246
(58) Field of Search .............................. 604/34, 36, 131, 604/132, 134, 153, 183, 185, 212, 216, 214, 245–247, 250, 256, 891.1

(56) References Cited

U.S. PATENT DOCUMENTS

| | | |
|---|---|---|
| 4,236,516 A | 12/1980 | Nilson |
| 5,011,477 A | 4/1991 | Winchell et al. |
| 5,080,652 A | 1/1992 | Sancoff et al. |
| 5,084,021 A | 1/1992 | Baldwin |
| 5,152,753 A | 10/1992 | Laguette et al. |
| 5,224,934 A | 7/1993 | Payne et al. |
| RE35,187 E | 3/1996 | Gortz |
| 5,505,707 A | 4/1996 | Manzie et al. |
| 5,807,312 A | 9/1998 | Dzwonkiewicz |
| 5,810,783 A | 9/1998 | Claro |
| 5,891,102 A | 4/1999 | Hiejima et al. |
| 5,906,597 A | 5/1999 | McPhee |
| 6,045,533 A | 4/2000 | Kriesel et al. |
| 6,206,850 B1 | 3/2001 | O'Neil |
| 6,213,972 B1 | 4/2001 | Butterfield et al. |
| 6,213,981 B1 | 4/2001 | Hiejima et al. |
| 2002/0019608 A1 | 2/2002 | Mason et al. |

FOREIGN PATENT DOCUMENTS

| | | |
|---|---|---|
| EP | 0 941 741 A | 9/1999 |
| WO | WO 87/00758 A | 2/1987 |
| WO | WO 00/71190 | 11/2000 |

*Primary Examiner*—Manuel Mendez
(74) *Attorney, Agent, or Firm*—Klein, O'Neill & Singh, LLP; Howard J. Klein (57) ABSTRACT

A patient controlled liquid drug administration device comprises a reciprocating pump having an inlet connectable to a source of a pressurized liquid drug, and an outlet connectable to the patient. A clamp rotates between closed and open positions respectively blocking and enabling pump outflow. A plunger above the pump has an end contacting a movable wall of the pump and is movable between raised and lowered positions. A button above the plunger moves between extended and depressed positions, and has a ledge that engages the clamp when the button is moved to the depressed position and moves the clamp to its open position. A compression spring is disposed between the plunger and the button. A spring catch engages a detent in the button when the button is moved to its depressed position and holds the button there until released by a catch release on the plunger that disengages the spring catch from the detent in the button when the plunger is moved to its lowered position. A removable tab permits easy, rapid priming of the pump by holding the clamp in its open position regardless of the position of the button, and by holding the button in its depressed position regardless of the position of the plunger.

13 Claims, 6 Drawing Sheets fig. 4 fig. 5 fig. 6

PATIENT CONTROLLED DRUG ADMINISTRATION DEVICE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO APPENDIX

Not Applicable

BACKGROUND OF THE INVENTION

1. Field of the Invention

This invention relates to medical devices in general, and in particular, to a patient controlled device for the self-administration of drugs, such as analgesics, and the like.

2. Description of Related Art

The treatment of pain symptoms, e.g., post-operative pain or pain resulting from disease or injury, frequently entails the subcutaneous and/or intravenous ("IV") infusion of a liquid analgesic and/or anesthetic drug into the patient, e.g., by one or more hypodermic injections thereof. When pain is more chronic, it may be preferable to catheterize the patient intravenously, e.g., with a hypodermic needle, and infuse the drug through the catheter continuously at a low, or "basal," rate of flow using, e.g., an "IV drip" or an electromechanical pump having an adjustably low flow rate.

Many patients who exhibit chronic pain symptoms also experience periodic episodes in which the pain level is perceived as much more acute, indicating a need for a temporarily greater infusion rate of the drug. To effect this, it is necessary to adjust the flow rate of the infusion apparatus, which in turn, necessitates the presence and intervention by a trained health care professional, as the patient typically lacks the training, skill and/or physical ability to effect such an adjustment of the infusion device.

In light of the foregoing, there have been a number of proposals for a "Patient Controlled Analgesic," or "PCA," drug administration device that would enable a patient to self-administer a drug intravenously without intervention by a health care professional at, e.g., the onset of an acute pain episode, that is not only simple and effortless to operate, but is also failsafe in use, i.e., one that precludes the possibility of a self-administered drug overdose. Examples of such PCA devices can be found in U.S. Pat. No. 5,084,021 to B. Baldwin; U.S. Pat. No. 5,891,102 to K. Hiejima et al.; and U.S. Pat. No. 6,213,981 to K. Hiejima et al.

These devices all have in common the provision of a reciprocating pump in which the patient manually effects a "compression" stroke of the pump by depressing a plunger of the pump, thereby expressing a measured bolus of a liquid drug to the patient intravenously, after which a compression spring and/or a pressurized source of the drug returns the plunger to its initial position, thereby effecting a refill, or "intake," stroke of the pump. The rate at which the pump refills, and hence, the rate at which the patient may self-administer the drug, is limited by a flow restrictor placed at the inlet of the pump. A reverse flow of fluids from the patient to the pump may be effected by a check valve disposed at the outlet of the pump.

While the foregoing PCA devices afford a partial solution to the problem of a patient controlled drug administration device, they also include certain drawbacks. For example, some require that the patient continuously exert a force on the plunger throughout the compression stroke of the pump, which may take several seconds or even minutes to complete, and some patients may not be physically capable of such a prolonged exertion. Others require that the patient push a first button down on the pump to effect the compression stroke, then push a second button on the pump to initiate the intake stroke, which may also be of prolonged duration, after the compression stroke is complete, which requires that the patient monitor the position of the plunger to know when to push the second button. An additional drawback shared by all is that they require an extended period of time, and require a careful manipulation of the device by a health care professional, to "prime" the device before use, i.e., to replace any air in the device with the liquid drug, since the administration of any air bubbles to the patient could form a dangerous embolism in the patient.

A need therefore exists in the medical field for a PCA device that can administer either or both of a continuous and a bolus infusion of a liquid drug to a patient, in which the bolus doses can be safely self-administered by the patient by quickly depressing a single button, to effect the compression stroke of the pump, and which thereafter automatically initiates the intake stroke of the pump when the compression stroke is completed, and further, one which can be rapidly primed for use without skilled manipulation of the device.

BRIEF SUMMARY OF THE INVENTION

In accordance with one aspect of the present invention, a PCA device is provided that enables either or both of a continuous flow of a liquid drug, as well as successive, large-volume boluses thereof, to be self-administered to and by a patient. The patient self-administers a single bolus of the drug by a quick push of a button that effects an extended-duration output stroke of a pump, so that the patient is not required to push the button down continuously during the output stroke, and the intake stroke of the pump is automatically effected at the end of the compression stroke by the device itself, without need for further monitoring or action by the patient. In another aspect of the invention, the novel device can be primed for use rapidly and without skilled manipulation thereof.

In one exemplary preferred embodiment thereof, the novel PCA device of the invention comprises an elongated housing having an axial cavity extending through it with a reciprocating pump mounted at a bottom end thereof. The pump defines a closed internal reservoir and includes a first wall, or seat, that is fixed in the cavity, and a second, flexible wall that is axially movable in the cavity in relation to the fixed wall between reservoir-full and reservoir-empty positions. The pump includes an inlet port that is connectable to a source of a pressurized liquid drug by an inlet conduit, and an outlet port subcutaneously connectable to the patient by an outlet conduit, both conduits extending out the bottom end of the housing. In one preferred embodiment, the inlet and outlet ports of the pump are arranged on the device such that, in a selected priming orientation of the device, the outlet port is disposed higher than the inlet port for rapid priming of the device.

A clamp is rotatably mounted in the cavity to move between a closed position constricting the outlet conduit of the pump, thereby preventing the flow of the liquid drug through the conduit, and hence, the flow of the drug from the pump, and an open position disengaged from the outlet conduit, thereby allowing the flow of the drug from the pump. The clamp is resiliently biased toward its closed position by a spring.

An elongated plunger is captivated in the cavity above the pump for axial movement between raised and lowered positions and has a lower end contacting the movable wall of the pump. An elongated push button is also captivated in the cavity above the plunger for axial movement between extended and depressed positions. The button includes a detent in it for latching the button in its depressed position, and a ledge that engages the clamp and moves it to its open position when the button is moved to its depressed position. In one exemplary embodiment of the device, the button includes an axial bore in a lower end portion thereof in which an upper portion of the plunger is coaxially disposed for relative axial sliding movement. A compression spring is axially disposed between the plunger and the button.

A spring catch mounted in the cavity of the housing resiliently engages the detent in the button when the button is moved to its depressed position, and holds the button there against the upward urging of the compression spring, until a catch release on the plunger disengages the spring catch from the detent in the button when the plunger is moved to its lowered position.

An optional bypass conduit can be provided in the device that connects the inlet conduit upstream of the pump to the outlet conduit downstream of the clamp, so that a continuous, or basal, flow of the liquid drug can be administered to the patient independently of pump or patient activity. An orifice may be inserted in the inlet conduit of the pump to regulate the rate of flow of the liquid drug into the pump, and hence, the rate at which the patient can safely self-administer the drug. Additionally, an orifice may be inserted in the bypass conduit for regulating the rate of basal flow of the liquid drug to the patient.

In another exemplary preferred embodiment of the PCA, the device is provided with a removable priming tab that extends through a side wall of the housing and engages both the clamp and a locking finger on the button such that the clamp is held in its open position regardless of the position of the button, and the button is held in its depressed position regardless of the position of the plunger. The priming tab enables the device to be primed rapidly and effortlessly by moving the push button to its depressed position, placing the device in the selected priming orientation, and connecting the inlet conduit to a source of pressurized liquid drug. After the device is primed and ready for use, the priming tab is simply removed and discarded.

A better understanding of the above and many other features and advantages of the novel PCA device may be obtained from a consideration of the detailed description of the invention below, particularly if such consideration is made in conjunction with the appended drawings.

BRIEF DESCRIPTION OF THE SEVERAL VIEWS OF THE DRAWINGS

FIG. 15 is an inboard elevation view of the device similar to that of FIG. 10; and, FIG. 16 is an exploded perspective inboard elevation view of the device.

DETAILED DESCRIPTION OF THE INVENTION

Figure 1:
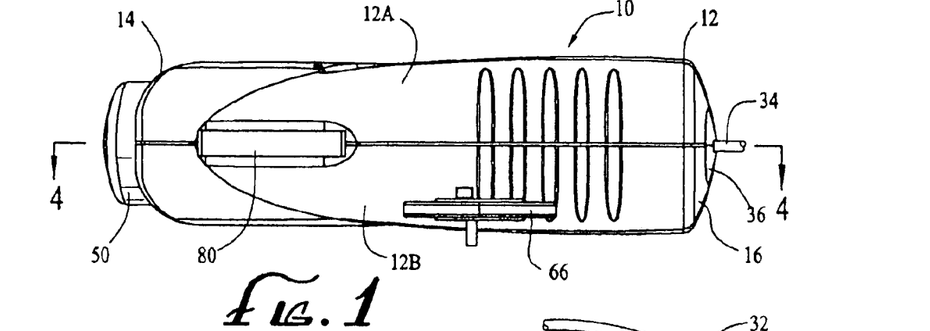
FIG. 1 is an elevation view of an exemplary preferred embodiment of a patient controlled liquid drug administration device in accordance with the present invention.

An exemplary preferred embodiment of a patient controlled liquid drug administration ("PCA") device 10 in accordance with the present invention is illustrated in the elevation view of FIG. 1. The device 10 comprises an elongated housing 12 having respective open top and bottom ends 14 and 16 and, as illustrated in, e.g., FIG. 7, an axial cavity 18 extending through it. In the particular exemplary embodiment illustrated in the figures, the housing is injection molded from a rugged plastic material, and includes two clam-shell side walls 12A and 12B that are coupled together, e.g., with an adhesive, along a medial plane extending through the device.

Figure 4:
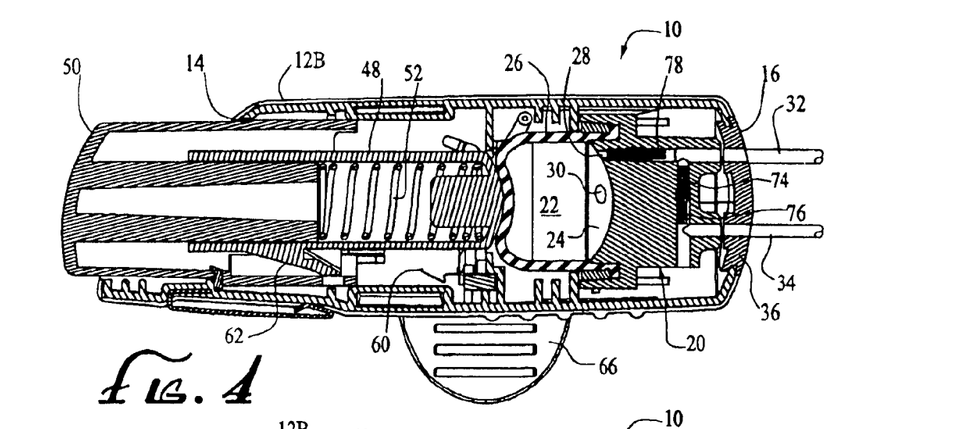
FIG. 4 is a cross-sectional side view of the device revealed by a section taken in FIG. 1 along the lines 4—4 therein, and showing the relative positions of the elements of the device at a point just before an output stroke of the pump is commenced, wherein a push button, the plunger and a movable wall of the pump are shown in respective extended, raised and reservoir-full positions thereof, and wherein a priming tab of the device is shown extending through an aperture in a side wall of a housing of the device and holding the clamp in an open position thereof.
Figure 5:
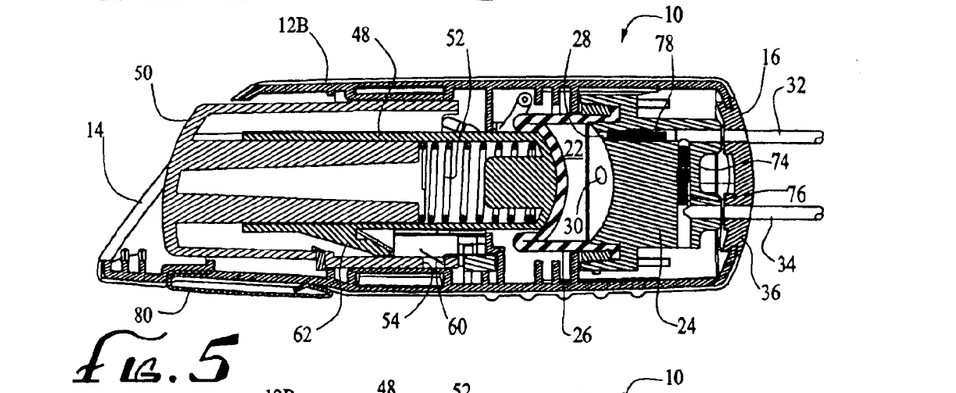
FIG. 5 is a cross-sectional side view of the device similar to that of FIG. 4, except showing the relative positions of the elements of the device at a point about midway through the output stroke of the pump, and wherein the button of the device is shown latched in a depressed position thereof.
Figure 6:
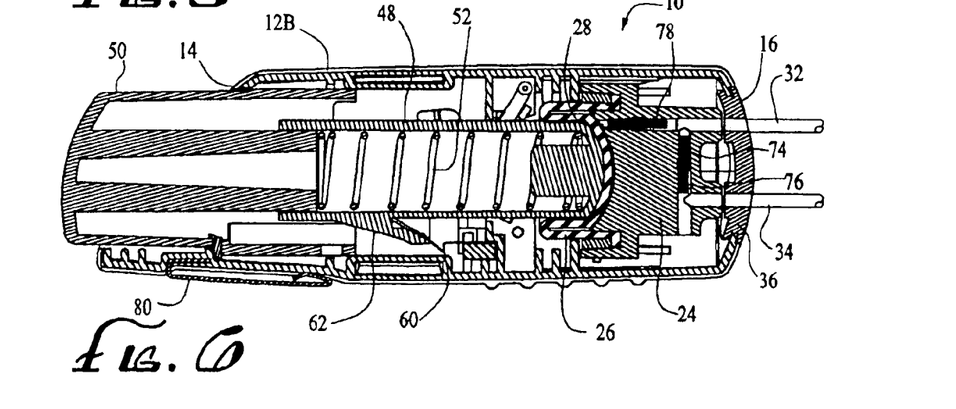
FIG. 6 is a cross-sectional side view of the device similar to those of FIGS. 4 and 5, except showing the relative positions of the elements of the device just after the output stroke of the pump is completed, wherein the plunger and movable wall of the pump are shown in respective lowered and reservoir-empty positions thereof, and wherein the button of the device is shown having automatically returned to the extended position thereof.

As shown in the cross-sectional views of FIGS. 4–6, a reciprocating pump 20 is mounted in the cavity 18 of the housing 12 at the bottom end 16 thereof. The pump defines a closed reservoir 22 for a liquid drug, and includes a first wall, or seat, 24 that is fixed in the cavity against movement, and a second, flexible wall 26 that is axially movable in the cavity with respect to the fixed wall between a reservoir-full position (see FIG. 4), and a reservoir-empty position (see FIG. 6).

The pump 20 includes an inlet port 28 and an outlet port 30. One end of an inlet conduit 32 is connected to the inlet port and the other end is connectable, e.g., by means of a Luer fitting (not illustrated), to a source of a pressurized liquid drug (not illustrated), which may comprise, e.g., an electromechanical infusion pump of a known type. The outlet port is subcutaneously connectable, e.g., by a hypodermic needle (not illustrated) to the patient by an outlet conduit 34. In one preferred embodiment, the inlet and outlet conduits comprise clear, flexible surgical tubing, and extend out the bottom end 16 of the housing 12 through a protective, flexible grommet 36.

A clamp 38 is mounted in the cavity 18 to move between a closed position constricting the outlet conduit 34 (see FIGS. 10 and 15), thereby preventing the flow of liquid through the conduit, and an open position disengaged from the outlet conduit (see FIGS. 7 and 9), thereby allowing the flow of liquid through it. A spring 40 resiliently biases the clamp toward its closed position. It may be seen that closing the clamp blocks the outflow of the pump 20 so that the reservoir 22 takes in, or refills with, the pressurized liquid drug through the inlet port 28 of the pump, and that opening the clamp enables the pump to expel the contents of the reservoir through the outlet port 30 of the pump.

Figures 15, 16:
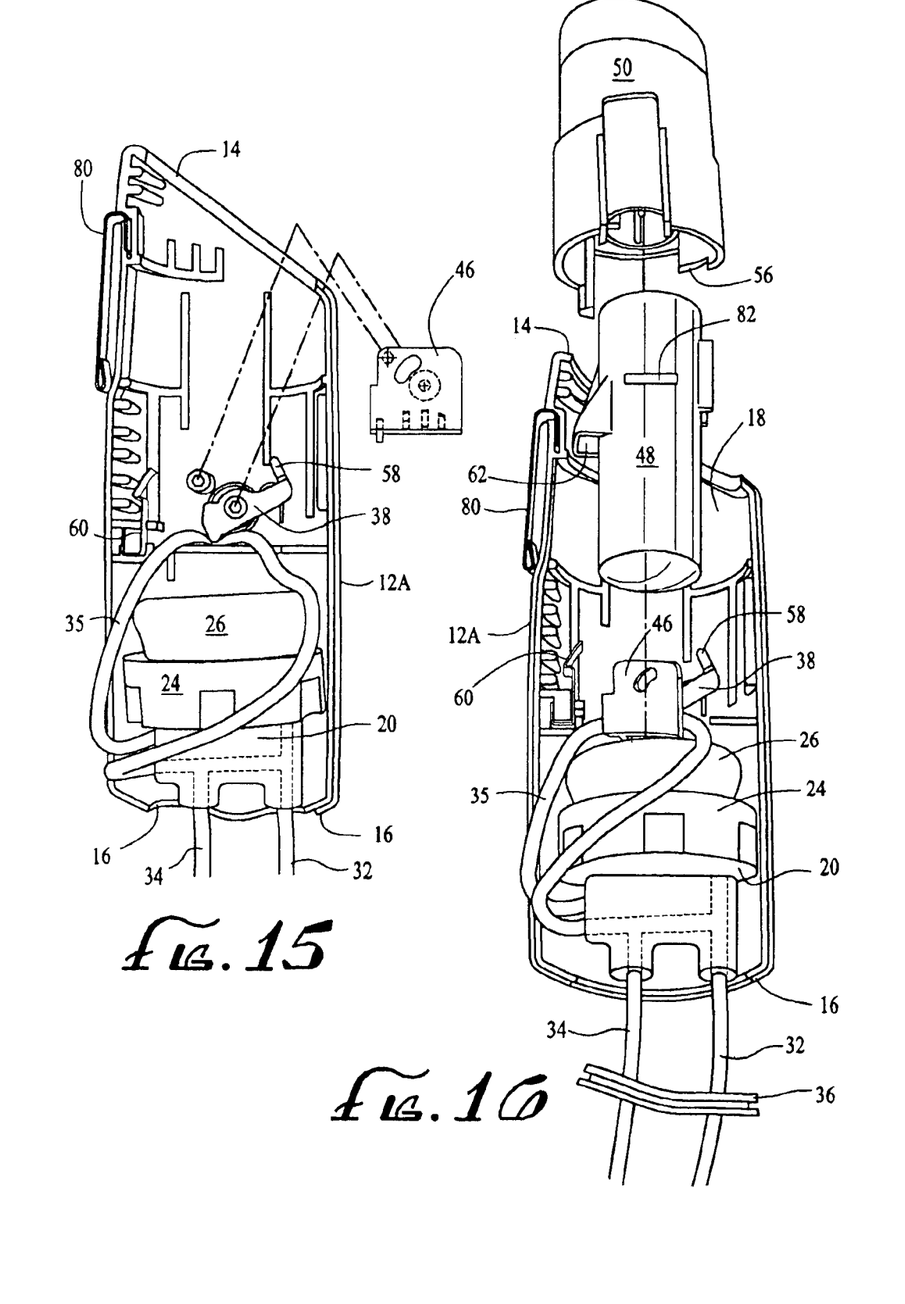

In the particular exemplary embodiment illustrated in the figures, the clamp 38 comprises a lever arm that is rotatably mounted on the side wall 12B of the housing 12 for movement between its closed and opened positions, and includes a wedge-shaped jaw 42 that constricts the outlet conduit 34 against an arcuate anvil 44 on the side wall, over which a loop 35 of the outlet conduit that is external to the pump 20 and internal to the housing is led (see FIGS. 15 and 16). A clamp shield 46 (see FIGS. 14A, 14B and 16) serves to capture the internal portion of the outlet conduit on the anvil and to journal the clamp for rotational movement.

As illustrated in the cross-sectional views of FIGS. 4–6, an elongated plunger 48 is captivated in the cavity 18 of the housing 12 above the pump 20 for axial movement between a raised position (see FIG. 4), and a lowered position (see FIG. 6). The plunger has a lower end 50 that contacts the movable wall 26 of the pump, and which has a shape that conforms to the internal shape of the fixed wall, or seat, 24 thereof. It may be seen that, if the clamp 38 is in its open position, a downward force exerted on the plunger will cause the plunger to move down from the raised position (see FIG. 4), and thereby push the movable wall of the pump toward the fixed wall thereof (see FIG. 5), until the movable wall conformably seats against the fixed wall (see FIG. 6), thereby executing an output stroke of the pump and expelling a bolus of liquid drug from the reservoir 22 of the pump to the patient. It may further be seen that, if the clamp is then closed, the pressurized source of the drug will begin to fill the reservoir with a new bolus of the drug, as above, causing the movable wall to move away from the fixed wall, and conjointly raising the plunger back up to its original, raised position, as described above.

The plunger 48 is pushed down by the patient indirectly through the agency of an elongated push button 50 that is captivated in the cavity 18 of the housing 12 above the plunger for axial movement between an extended position (see FIGS. 4 and 6) and a depressed position (see FIG. 5), as well as a compression spring 52 that is axially disposed between the plunger and the button. In the particular exemplary embodiment illustrated in the figures, the button includes an axial bore extending through a lower end thereof, and an upper portion of the plunger is coaxially disposed in the bore for relative sliding axial movement therein, thereby captivating the compression spring and resulting in a more compact device 10.

Figure 9:
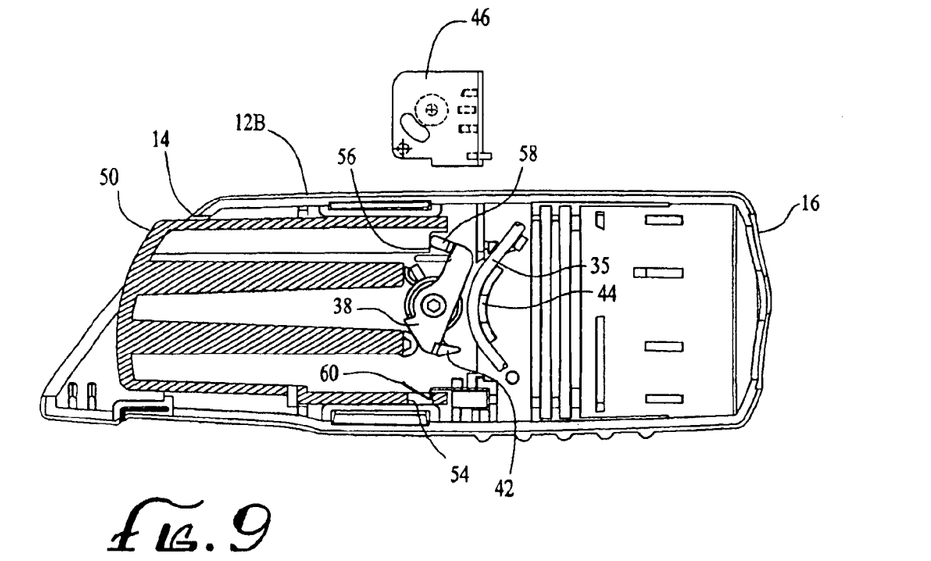
FIG. 9 is a partial cross-section and inboard side elevation view of the device similar to that of FIG. 7, wherein the button is shown latched in its depressed position and a clamp shield is shown removed from the device to reveal a ledge on the button engaging the clamp and holding it in its open position disengaged from the outlet conduit.
Figure 10:
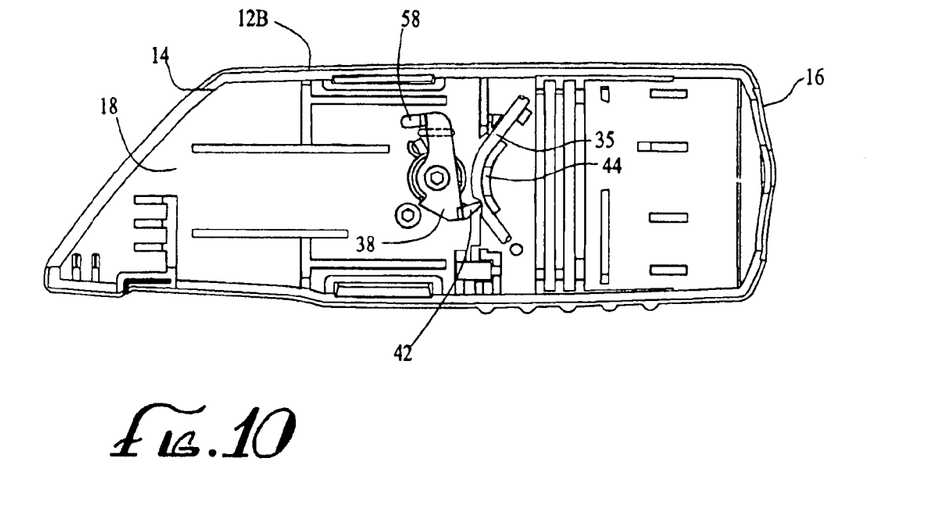
FIG. 10 is an inboard elevation view of the device similar to that of FIG. 9, showing the button removed and a spring biasing the clamp into its closed position in constricting engagement with the outlet conduit.

The button 50 includes a detent 54 for latching the button in the depressed position, and a ledge 56 that engages the clamp 38 and moves it to its open position when the button is moved to its depressed position, as illustrated in FIG. 9. As shown in FIG. 9, when the button (shown in cross-section) is pushed to its depressed position, the ledge of the button engages an extension 58 on the lever arm of the clamp and rotates it to its open position, thereby enabling outflow from the pump 20, as described above. Simultaneously, the latching detent engages a resilient spring catch 60 mounted in the cavity 18 in an over-center latching engagement, which holds the button in its depressed position and against the upward force of the compression spring 52.

Movement of the button 50 to its depressed position also compresses the compression spring 52 against the plunger 48 (see FIG. 5), resulting in a corresponding downward movement of the plunger against the movable wall 26 of the pump 20 and a corresponding output stroke of the pump, as described above. Thus, a single, quick depression of the button to its depressed position by the patient results in a subsequent full output stroke of the pump that is typically of an extended duration, due to the flow resistance in the device between the pump and the patient. However, since the button latches in the depressed position, as above, it is unnecessary for the patient to exert a continuous force on the button for the entire duration of the stroke.

To enable the button 50 to return automatically to its extended position at the end of the output stroke of the pump 20 (see FIG. 6), a scoop-like catch release 62 is provided on the plunger 48 that catches an end of the spring catch 60 and detaches it from the latching detent 54 in the button when the plunger reaches its lowered position. When the button returns to its extended position, the compression in the compression spring 52 is relaxed, and simultaneously, the clamp 38 is released to return to its closed position, thereby initiating an intake stroke of the pump, as described above. Thus, the intake stroke of the pump is effected automatically, and no activity or monitoring of the device 10 is required on the part of the patient.

Figure 3:
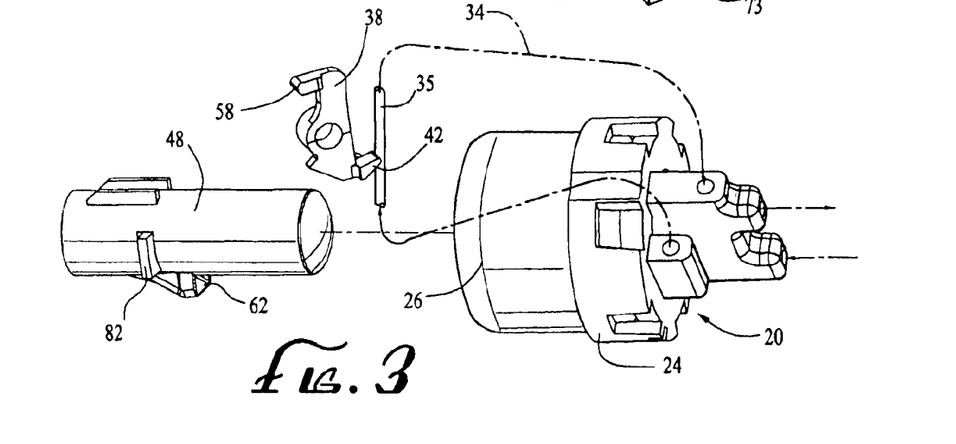
FIG. 3 is a partial exploded perspective view of a plunger, reciprocating pump, clamp and outlet conduit of the device, wherein the clamp is shown in a closed position thereof and in constricting engagement with the outlet conduit.
Figure 8:
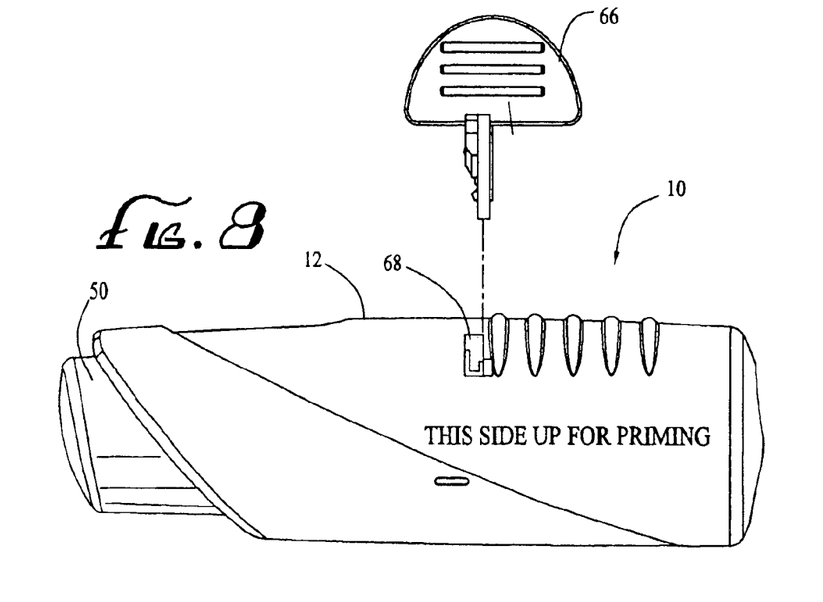
FIG. 8 is a side elevation view of the device showing the priming tab removed from the device.

In another preferred embodiment, the PCA device 10 of the present invention can be primed for use in a procedure that is both rapid and simple. As illustrated in FIGS. 3–5, the respective inlet and outlet ports 28 and 30 of the pump 20 are arranged on the device such that, in a selected, resting orientation of the device, the outlet port is disposed higher than the inlet port, so that any air bubbles in the liquid drug in the reservoir 22 are directed toward the outlet port by gravity. This is effected by simply laying the device 10 on its side on, e.g., a table, such that the outlet port is higher than the inlet port, as shown in FIG. 8. The legend, "THIS SIDE UP FOR PRIMING," can be applied to the upstanding side, as shown, as an aid to the practitioner.

Figure 7:
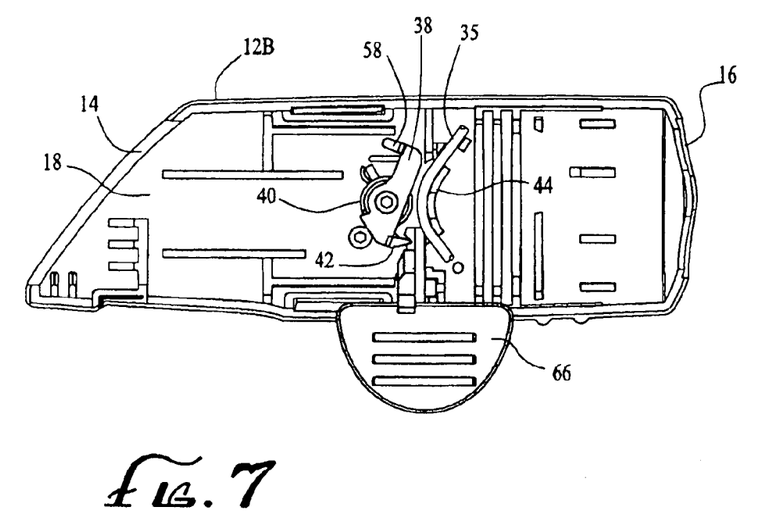
FIG. 7 is a inboard elevation view of the device similar to that of FIG. 4, with a part of the housing, pump, plunger and button of the device removed to reveal the clamp and a portion of the outlet conduit thereof, and wherein the priming tab is shown holding the clamp in its open position and disengaged from the outlet conduit.
Figures 11A, 11B, 11C, 12A, 12B, 13A, 13B, 13C, 14A, 14B:
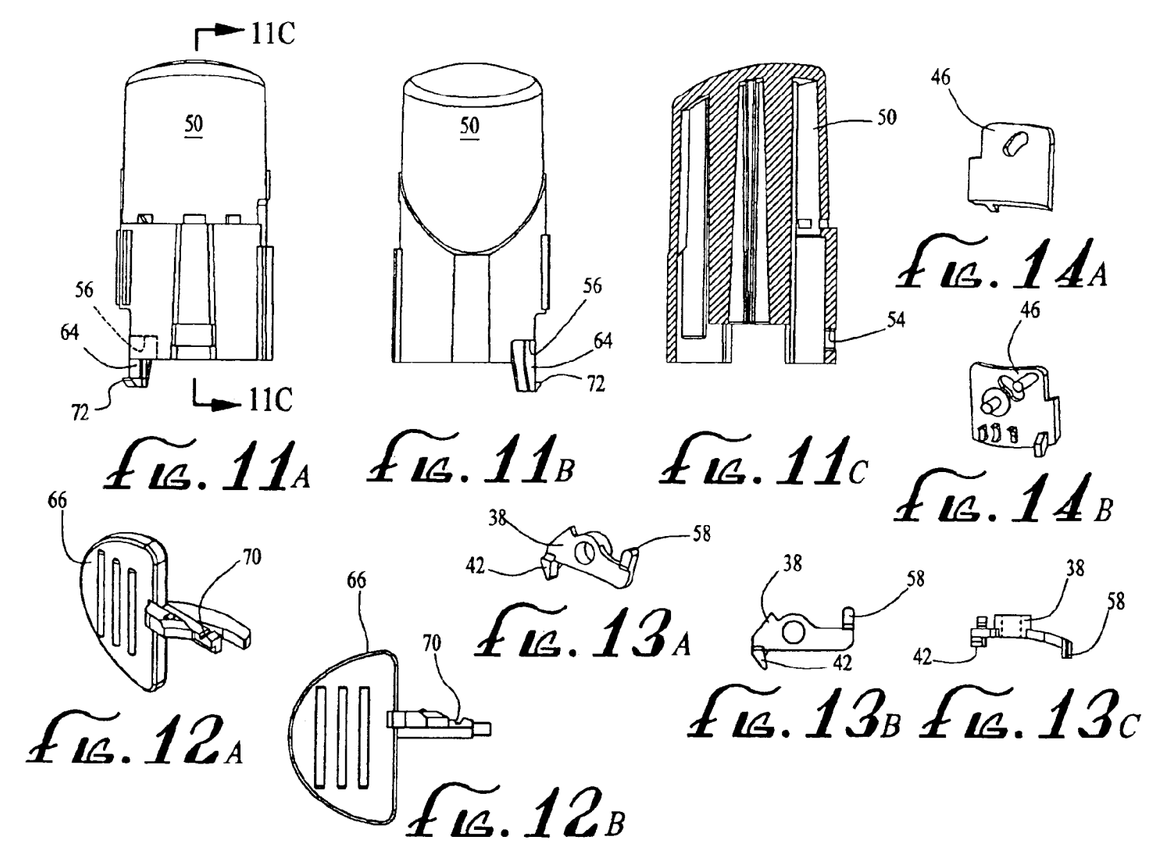
FIGS. 11A–11C are respectively front and rear elevation views of the button, and a cross-section view thereof, as revealed by the section taken in FIG. 11A along the lines 11C—11C.
FIGS. 12A and 12B are respectively front side perspective and front plan views of the priming tab.
FIGS. 13A–13C are respectively front side perspective, front plan and bottom plan views of the clamp.
FIGS. 14A and 14B are respectively front and rear perspective views of the clamp shield.

As illustrated in FIGS. 11A and 11B, a resilient locking finger 64 is provided on the button 50, and as illustrated in FIGS. 7 and 8, a removable priming tab 66 is inserted through an aperture 68 in a side wall of the housing 12 that engages both the clamp 38 and the locking finger of the button such that the clamp is held in its open position regardless of the position of the button, and such that the button is held in its depressed position regardless of the position of the plunger 48. To this end, the priming tab includes a notch 70 (see FIGS. 12A, 12B) that engages the wedge-shaped jaw 42 of the clamp and holds it in its open position, as shown in FIG. 7, even when the button is up, or in its extended position. This arrangement provides an additional benefit in that, if the device 10 is stored in inventory for an extended period before use, the priming tab prevents the clamp from forming a permanent constriction in the flexible outlet conduit 34 during such storage.

The resilient locking finger 64 on the button 50 includes a ramped tooth 72 (see FIG. 11A) that slides over and catches on the priming tab 66 when the button is pushed down to its depressed position. Thus, even though the button conjointly pushes the plunger 48 to its lowered position such that the catch release 62 of the plunger disengages the spring catch 60 from the latching detent 54 in the button, the button remains in its depressed position, and hence, the plunger is correspondingly held in its lowered position. The foregoing arrangement results in both the clamp 38 being held in its open position, and the volume of the reservoir 22 of the pump 20 being reduced to its minimum size, i.e., to the narrow space between the fixed wall 24 and the movable wall 22 of the pump, as shown in FIG. 6. In this configuration, the pump can be quickly primed using only a very small quantity of the liquid drug.

Thus, in a preferred embodiment of the device 10, the device is manufactured, stored and supplied with the priming tab 66 inserted in place. The device is then primed rapidly and with a minimum of manipulation of the device by: 1) removing the device from any sterile packaging; 2) moving the push button 50 to its depressed position; 3) placing the device on a surface or holding it in the selected priming orientation ("THIS SIDE UP FOR PRIMING"); and, 4) connecting a distal end of the inlet conduit 32 to a source of pressurized liquid drug. The liquid drug quickly fills the inlet conduit and the minimized volume of the reservoir 22 of the pump 20, and pushes any air therein ahead of it and out of the elevated outlet port 30 and the outlet conduit 34. After the device is primed, the priming tab is simply removed and discarded, whereupon the button returns to its extended position, the clamp 38 closes the outlet conduit, and reservoir begins to fill with an initial bolus of the drug. A tubing clamp 73 of a known type (see FIG. 2) can be provided on the outlet conduit to control the flow of the liquid drug through the device during the priming operation.

As will be seen from the above, the PCA device 10 enables a patient to self-administer successive, large-volume boluses of a liquid drug. Additionally, as illustrated in FIGS. 4–6, the device can also be made capable of administering a continuous, basal flow of the drug independently of patient control by the provision of a bypass conduit 74 on the pump 20 which has a first end connected to the inlet conduit 32 upstream of the pump and an opposite second end connected to the outlet conduit 34 downstream of the clamp 38. The flow of the liquid drug through the bypass conduit 74 bypasses the reservoir 22 of the pump and is thus administered directly to the patient through the outlet conduit. A flow restrictor 76, e.g., a glass orifice, can be provided in the bypass conduit for regulating the rate of basal or continuous flow of the liquid drug to the patient.

Additionally, or alternatively, a second flow restrictor 78 can be provided in the inlet conduit 32 of the pump 20 for regulating the rate at which the liquid drug refills the pump, and therefore, the maximum rate at which the patient can self-administer successive boluses of the drug, thereby precluding the possibility of a self-administered overdose thereof.

As will by now be evident to those of skill in this art, many variations and modifications are possible in the materials and methods of the PCA device 10 of the present invention without departing from its essence and scope.

Figure 2:
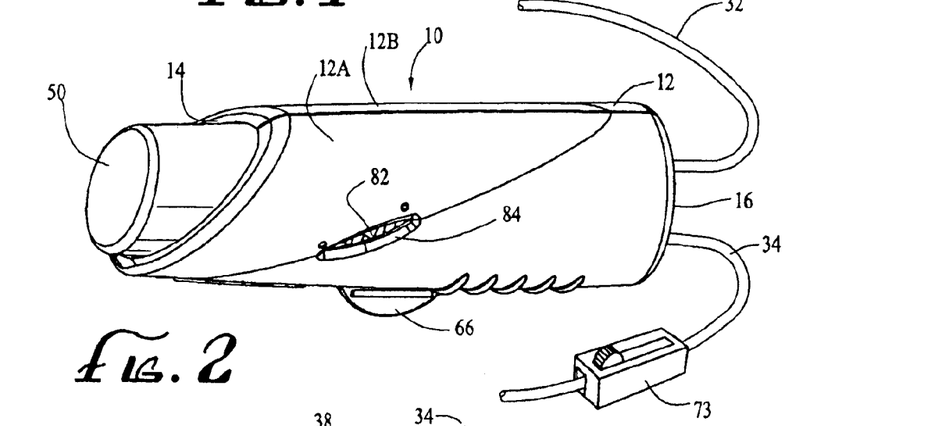
FIG. 2 is a top and side perspective view of the device.

For example, as illustrated in FIG. 1, a resilient clip 80 can be provided on the housing 12 of the device 10 so that the device can be conveniently attached to an article of the patient's clothing or bed clothes. Additionally, as illustrated in FIG. 2, an indicator 82 can be provided on the plunger 48, and a corresponding window 84 can be formed in the housing 12 of the device through which the indicator may be seen, such that the axial position of the plunger relative to its raised (reservoir-full) and lowered (reservoir-empty) positions can be easily visualized through the housing.

In light of the foregoing examples, the scope of the present invention should not be limited to that of the particular embodiments described and illustrated herein, as these are merely exemplary in nature. Rather, the scope of the present invention should be commensurate with that of the claims appended hereafter and their functional equivalents.

What is claimed is:

1. A new patient controlled liquid drug administration device, comprising:

a housing defining an axial cavity having inner and outer ends;

a pump mounted near an inner end of the cavity, the pump defining a reservoir having a first wall fixed in the cavity and a second wall flexibly movable therein with respect to the first wall between reservior-full and reservoir-empty positions;

an inlet conduit having a first end connected to an inlet port of the pump and a second end connectable to a source of pressurized liquid drug;

an outlet conduit having a first end connected to an outlet port of the pump and an opposite second end subcutaneously connectable to the patient;

a clamp mounted in the cavity to move between a closed position constricting the outlet conduit and thereby preventing the flow of liquid through it, and an open position disengaged from the outlet conduit, thereby allowing the flow of liquid through it, the clamp being biased toward its closed position;

a plunger engageable with the second wall of the reservoir and disposed for axial movement within the cavity between the first position in which the second wall is in the reservoir-full position and a second position in which the second wall is in the reservoir-empty position;

a plunger-actuating button extending from the outer end of the cavity and disposed in the cavity for axial movement between extended and depressed positions, the button having a detent for and a ledge that engages the clamp and moves it to its open position when the button is moved to its depressed position;

a spring under compression disposed between the plunger and the button;

a spring catch mounted in the cavity that resiliently engages the detent in the button when the button is moved to its depressed position and holds the button in its depressed position against the force of the spring; and a catch release on the plunger that disengages the spring catch from the detent in the button when the plunger is moved to its second position.

2. The device of claim 1, further comprising:

a locking finger on the button; and a removable priming tab extending through a side wall of the housing that engages both the clamp and the locking finger of the button such that the clamp is held in its open position regardless of the position of the button, and the button is held in its depressed position regardless of the position of the plunger.

3. The device of claim 1, further comprising a bypass conduit having a first end connected to the inlet conduit upstream of the pump and an opposite second end connected to the outlet conduit downstream of the clamp, whereby a continuous flow of the liquid drug can be administered to the patient independently of patient control.

4. The device of claim 3, further comprising a flow restrictor in the bypass conduit for regulating the rate of continuous flow of the liquid drug to the patient.

5. The device of claim 3, further comprising:

a locking finger on the button; and a removable priming tab extending through a side wall of the housing that engages both the clamp and the locking finger of the button such that the clamp is held in its open position regardless of the position of the button, and the button is held in its depressed position regardless of the position of the plunger.

6. The device of claim 1, further comprising a flow restrictor in the inlet conduit of the pump for regulating the rate of flow of the liquid drug into the pump.

7. The device of claim 1, further comprising an adjustable conduit clamp between the first and second ends of the outlet conduit.

8. The device of claim 1, wherein the clamp comprises a lever arm rotatably mounted in the cavity for movement between its closed and opened positions.

9. The device of claim 1, wherein the button includes an axial bore extending through an inner end thereof, and wherein a portion of the plunger is coaxially disposed in the bore for relative axial movement therein.

10. The device of claim 1, further comprising an indicator on the plunger and a window in the housing through which the indicator may be seen, whereby the axial position of the plunger relative to its first and second positions can be ascertained through the housing.

11. In a patient controlled liquid drug administration device of a type that includes a reciprocating pump, a plunger engageable with the pump, and a push button engageable with the plunger, the improvement in combination therewith comprising:

means operatively responsive to movement of the push button between extended and depressed positions thereof for respectively closing and opening an outlet of the pump;

means for releasably latching the push button in the depressed position thereof; and means operatively responsive to movement of the plunger to a selected position thereof for releasing the push button form the depressed position thereof.

12. The device of claim 11, wherein the improvement further comprises:

means removable from the device for temporarily holding the outlet of the pump open regardless of the position of the push button, and for holding the push button in the depressed position thereof regardless of the position of the plunger.

13. The device of claim 12, wherein the improvement further comprises:

the outlet of the pump being disposed higher than an inlet of the pump in a selected resting orientation of the device.

* * * * *